United States Patent [19]

Napier et al.

[11] 4,066,719

[45] Jan. 3, 1978

[54] SELECTIVE PHOSPHORYLATION PROCESS

[75] Inventors: Roger P. Napier, Califon, N.J.; Orville L. Chapman, Los Angeles, Calif.

[73] Assignee: Mobil Oil Corporation, New York, N.Y.

[21] Appl. No.: 736,020

[22] Filed: Oct. 27, 1976

Related U.S. Application Data

[63] Continuation-in-part of Ser. No. 548,508, Feb. 10, 1975, Pat. No. 4,003,966.

[51] Int. Cl.$^2$ .............................................. C07F 9/12

[52] U.S. Cl. ................................................... 260/970
[58] Field of Search ...................................... 260/970

[56] References Cited

U.S. PATENT DOCUMENTS 4,003,966  1/1977  Napier et al. ..................... 260/971

Primary Examiner—Anton H. Sutto
Attorney, Agent, or Firm—Charles A. Huggett

[57] ABSTRACT

A one step process for the preparation of phosphate esters of acidic hydroxy-containing compounds, e.g., phenols, by reacting said compounds with dimethyl disulfide and a trialkyl phosphite.

8 Claims, No Drawings

SELECTIVE PHOSPHORYLATION PROCESS

CROSS-REFERENCE TO RELATED APPLICATIONS

This application is a continuation-in-part of application, U.S. Ser. No. 548,508 filed Feb. 10, 1975, now U.S. Pat. No. 4,003,966.

BACKGROUND OF THE INVENTION

1. Field of the Invention

This invention is directed to a selective phosphorylation process. More particularly it is directed to a process of phosphorylating acidic hydroxy compounds, examples of which include phenols, enols, etc., by reacting such compounds with dimethyl disulfide and a trialkyl phosphite.

2. Description of the Prior Art

It is known that alcohols[1], mercaptans and thiophenols[2] maybe phosphorylated by reacting them with, for example, bromotrichloromethane or bromocyanoacetamide[3], and trimethyl phosphite. More recently phenols, oximes and enols have been phosphorylated in similar manner[4].

[1]A., J. Burn and J. I. G. Cadogan, J. Chem. Soc., 5788 (1963). P. C. Crofts and I. M. Downie, J. Chem. Soc., 2559 (1963).
[2]P. J. Bunyan and J. I. G. Cadogan, J. Chem. Soc., 2953 (1962). L. L. Murdock and T. L. Hopkins, J. Org. Chem., 33 907 (1968).
[3]T. Hata and T. Mukaiyama, Bull. Chem. Soc. Japan, 35 1106 (1962).
[4]R. P. Napier and S. T. D. Gough, [1]A. Preps. and Procedures Int., 3(3), 117 (1971) and British 1309 122.

Conventional methods to phosphorylate generally materials such as phenols include a two step reaction, as shown below. A phenol, e.g., phenol is first reacted with sodium carbonate to obtain sodium (phenoxide) which is then reacted in the second step to obtain the phosphate:

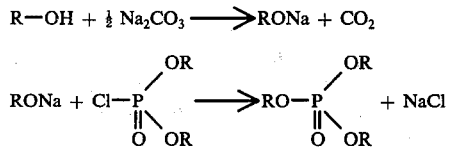

See G. M. Kosolapoff "Organophosphorus Compounds", John Wiley & Sons, Inc. New York, New York 1950.

SUMMARY OF THE INVENTION

In accordance with this invention a phosphorylation process is provided in which phosphate esters of acidic hydroxy compounds are prepared by reaction of such compounds with dimethyl disulfide and a trialkyl phosphite.

DESCRIPTION OF SPECIFIC EMBODIMENTS

Prior art phosphorylation procedures, previously referred to, did not discern the differences in reactivity between phenols and thiophenols. If a mixture of these reactants were phosphorylated, a corresponding mixture of phosphorylated products would be obtained.

However, we have discovered that the dimethyl disulfide-trialkyl phosphite reagent as embodied in this invention phosphorylates phenols but alkylates thiophenols. Thus, this invention can be used to prepare phenyl dialkylphosphates from phenols, and alkyl phenyl sulfides from thiophenols. This reaction is of particular value in the synthesis of p-methylthiophenyl dialkyl phosphates, e.g., p-mercaptophenol is S-alkylated and O-phosphorylated to p-methylthiophenyl-0,0-dimethyl phosphate with excellent selectivity by the dimethyl disulfide-trialkyl phosphite treatment, i.e. the OH group is phosphorylated in preference to the SH group which is alkylated in preference to the OH group. The present invention, therefore, describes a novel and improved method for phosphorylation of acidic hydroxy compounds such as phenols, enols, etc.

In accordance with this invention, dimethyl disulfide may be mixed with a trialkyl phosphite, e.g., trimethyl phosphite, to form a reactive complex.

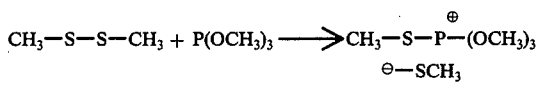

An acidic hydroxy compound, for example phenol, is then added to complete the reaction:

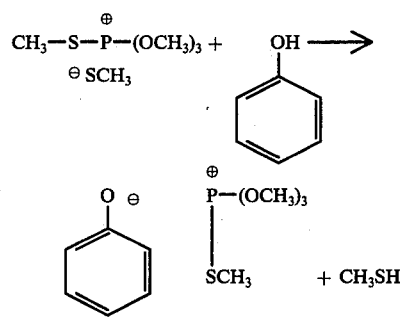

The complex thus produced reacts to form the final products:

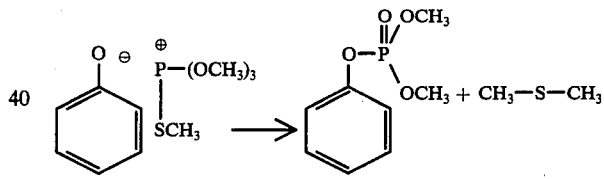

Although the initial reactive complex,

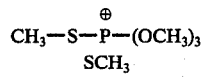

was proposed by H. I. Jacobsen, R. G. Harvey, and E. V. Jensen, J.A.C.S. 77, 6604 (1955), their reported reaction was as detailed below:

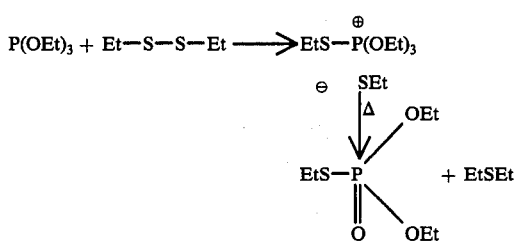

Furthermore, Jacobsen et al. did not utilize the complex per se in phosphorylation (of an added reactant) but rather heat decomposed it to form triethyl monothiophosphate. Alternatively, in practice of the present invention, the phenol may be dissolved in the dimethyl disulfide and the trialkyl phosphite then added dropwise to the resulting solution.

This invention is based upon our discovery that acidic hydroxy compounds, inclusive of phenols, substituted phenols, enols, etc. may be reacted in the above described manner to change the course of the expected reaction and selectively produce the desired phosphorylated products.

This invention therefore, provides, in specific embodiments, a process for the selective preparation of 0,0-dialkyl phosphates of phenols.

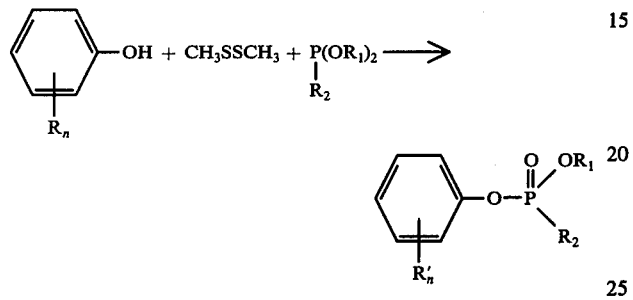

wherein R is selected from the group consisting of H, alkyl of 1-12 carbon atoms, nitro, nitroso, halo, carboxy, carbalkoxy, alkylmercapto and haloalkyl of 1-8 carbon atoms, hydroxymethyl, mercapto, N-hydroxyiminomethyl and $n$ is 1-5; $R_1$ is alkyl of 1-12 carbon atoms and $R_2$ is selected from the group consisting of alkyl of 1-12 carbon atoms, alkoxy, amino and mono or dialkylamino $C_1$-$C_{16}$ and wherein R' has the same significance as R except for mercapto. Accordingly, the process embodies reacting acidic hydroxy compounds, and particularly phenols, with the admixture of dimethyl disulfide and trialkyl phosphite each alkyl group of which has from 1-12 carbon atoms or adding trialkyl phosphite to a mixture of a phenol and dimethyl disulfide.

The reaction temperature may vary within wide limits, i.e. from room temperature to the boiling point of the reactants; however, a temperature of from about 30° to about 60° C has proven satisfactory.

In a more specific embodiment of this invention, the phosphorylation process is directed to producing compounds in which R' is H or $C_1$-$C_8$ alkylmercapto, in the product of the aforesaid preparation of 0,0-dialkyl phosphates of phenols, $R_1$ and $R_2$ are the same or different and are alkyl $C_1$-$C_8$ or more particularly methyl or ethyl.

Suitable trialkyl phosphites include trimethyl phosphite, triethyl phosphite, tributyl phosphite, trinonylphosphite, etc. Generally speaking, trialkyl phosphites having from 1-12 carbon atoms per alkyl group are preferable.

Representative phosphates prepared according to this invention include:
0,0-Diethyl-0-phenyl phosphate
0,0-Dimethyl-0-phenyl phosphate
0,0-Diisopropyl-0-phenyl phosphate
0,0-Dibutyl-0-phenyl phosphate,
0,0-Dipentyl-0-phenyl phosphate,
0,0-Diheptyl-0-phenyl phosphate
0-Ethyl,0-methyl-0-phenyl phosphate,
0,0-Dibutyl-0-(trichlorophenyl) phenyl phosphate,
0,0-Dimethyl-0-monochlorophenyl phosphate,
0,0-Diethyl-0-phenyl phosphate,
0,0-Dimethyl-0(p-chlorophenyl) phosphate,
0,0-Diethyl-0-(p-chlorophenyl) phosphate,
0,0-Dimethyl-0-(p-methylphenyl) phosphate,
0,0-Dimethyl-0-(4-benzo (b) thienyl) phosphate,
0,0-Dimethyl-0-(3-methoxyphenyl) phosphate,
0,0-Dimethyl-0-(p-methylthiophenyl) phosphate, etc.

Compounds of this type are useful as insecticides, for example, 0,0-Dimethyl-0-(4-methylthiophenyl) phosphate is a known effective insecticide described in U.S. Pat. No. 3,151,022.

SPECIFIC EXAMPLES

EXAMPLE I

PREPARATION OF 0,0-Dimethyl-0-Phenyl Phosphate

Trimethyl phosphite (6.2g, 0.05 mole) was mixed with 4.7g (0.05 mole) dimethyl disulfide. Phenol (4.7g 0.05 mole) was added in two equal portions. After each portion was added, an exotherm brought the reaction temperature to 35° C. The reaction mixture was warmed with a heat lamp to 50° C for 5 hours, and methyl mercaptan was evolved. Distillation afforded 6.4g (69% yield) of material with a b.p. of 88°-90° C at 0.1 mm. This material compared spectrally with authentic material prepared in the conventional manner.

EXAMPLE II

PREPARATION OF 0,0-Dimethyl-0-(p-methylthiophenyl) Phosphate p-methylthiophenol (7.0g, 0.05 mole) was dissolved in 5.0 g (0.053 mole) of dimethyl disulfide. Then 6.2g (0.05 mole) of trimethyl phosphite was added dropwise so as to control the exothermic reaction. After addition was complete, the reaction was warmed to 50° C for 1 hour. Solvents and by-products were removed on a rotating evaporator to afford a quantitative yield of product which exhibited an infrared spectrum which was identical to authentic product prepared in the conventional manner.[5]

[5] See U.S. 3,151,022

EXAMPLE III

PREPARATION OF 0,0-Dimethyl-0-(p-methylthiophenyl) Phosphate p-Mercaptophenol (12.6g, 0.10 mole) was dissolved in 20g (0.21 mole) of dimethyl disulfide. Then 24.8g (0.20 mole) of trimethyl phosphite was added dropwise so as to control the exothermic reaction at or below 45° C. The solution was then warmed to 50° C for one hour. After cooling to room temperature the solution was distilled to afford 15.1g (69% yield) of product (b.p. 138°-140° C at 0.1 mm). The product was identical to that obtained in the conventional manner.[5]

EXAMPLE IV

PREPARATION OF Methyl Phenyl Sulfide

Benzenethiol (11.0g, 0.10 mole) was dissolved in 9.4g (0.10 mole) of dimethyl disulfide and treated with 12.4g (0.10 mole) of trimethyl phosphite. The reaction solution was washed with aqueous sodium hydroxide and distilled to afford 11.1g (89%) of desired product. The infrared and nmr spectra were identical to that exhibited by authentic material.

EXAMPLE V

PREPARATION OF 0,0-Diisopropyl-0-(p-methylthiophenyl) Phosphate p-Methylthiophenol (7.0g, 0.05 mole) was dissolved in 6.0g (0.06 mole) of dimethyl disulfide and treated with 10.4g (0.05 mole) of triisopropyl phosphite and warmed to 50° C for 4 hours. Distillation afforded 7.6g (50% yield) of product with b.p. 136°–138° C at 1.1 mm. Infrared and nmr spectra confirmed the structure.

EXAMPLE VI

PREPARATION OF 0,0-Dimethyl-0-(p-chlorophenyl) Phosphate p-chlorophenol (12.9g 0.1 mole) was dissolved in 9.4g (0.10 mole) of dimethyl disulfide and treated with 12.4g (0.10 mole) of trimethyl phosphite. The exothermic reaction was controlled at 45° C by regulation of the rate of phosphite addition. After heating at 50° C for 2 hours, distillation afforded 17.0g (72% yield) of product with b.p. 103°–106° C at 0.07 mm. Infrared and nmr spectra confirmed the structure.

EXAMPLE VII

PREPARATION OF 0,0-Diethyl-0-Phenyl Phosphate

Phenol (9.4g, 0.1 mole) was dissolved in 10g (0.106 mole) of dimethyl disulfide and treated dropwise with 16.6g (0.10 mole) of triethyl phosphite so as to control the exotherm at 40° C. Distillation afforded 15.1g (69% yield) of product with b.p. 101° C at 0.12 mm. The product was identical in all respects to material prepared in the conventional manner.

EXAMPLE VIII

PREPARATION OF 0,0-Dimethyl-0-(p-Methylphenyl) Phosphate p-Cresol (10.8g, 0.1 mole) was dissolved in 9.4g (0.1 mole) of dimethyl disulfide and treated dropwise with 12.4g (0.1 mole) of trimethyl phosphite so as to control the exotherm at 40° C. Distillation at 99° C and 0.07 mm afforded 14.4g (67% yield) of product which exhibited the expected infrared and nmr spectra.

EXAMPLE IX

PREPARATION OF 0,0-Dimethyl-0-(4-benzo(b)thienyl) Phosphate

4-Hydroxybenzo(b)thiophene (15g, 0.1 mole) was dissolved in 9.4g (0.1 mole) of dimethyl disulfide and treated with 12.4g (0.1 mole) of trimethyl phosphite at 40° C. Distillation at 145° C and 0.07 mm afforded 17.4g (67% yield) of product which exhibited infrared and nmr spectra consistent with the assigned structure.

EXAMPLE X

PREPARATION OF 0,0-Dimethyl-0-(3-methoxyphenyl) Phosphate m-Methoxyphenol (12.4g, 0.1 mole) was dissolved in 9.4g (0.10 mole) of dimethyl disulfide. Then 12.4g (0.10 mole) of trimethyl phosphite was added dropwise so as to control the exotherm at 40° C. Distillation afforded 16.6g (77% yield) of product which had b.p. 119°–121° C at 0.10 mm. The infrared and nmr spectra of the product were consistent with the assigned structure.

The above examples illustrate the novel and unobvious aspects of the claimed process. For example, Examples I and VII illustrate straight-forward phosphorylation of a hydroxy group (phenol) to yield the dialkyl phosphate ester; Examples II and III illustrate that with different starting materials you can still obtain the same final product (process otherwise the same) due to the selectivity of the reagents embodied in the invention toward phosphorylation of hydroxy groups and alkylation of thiol groups; Example IV a straight-forward alkylation of a thio starting material to yield an alkyl phenol sulfide as disclosed supra; Example III also graphically illustrates that a p-mercaptophenol is selectively S-alkylated and O-phosphorylated via the process embodied by the herein disclosed invention.

Therefore, contrary to the prior art, which taught that a mixture of phosphorylated products would be obtained, the instant process achieves phosphorylation of materials such as phenols and alkylation of thiophenols providing for a one-step process of phosphorylating compounds highly useful in the agricultural chemistry art.

Although the present invention has been particularly described with respect to preferred embodiments, all the disclosed embodiments and modifications apparent to one ordinarily skilled in the art are considered to be within the scope of this invention.

What is claimed is:

1. A process for selective preparation of 0,0-dialkyl phosphates of phenols having the following general formula:

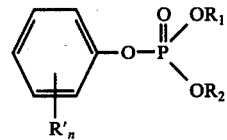

wherein R' is alkylmercapto and n is 1–5; $R_1$ is alkyl of 1–12 carbon atoms; and $R_2$ is alkyl of 1–12 carbon atoms, comprising reacting, from about room temperature to the boiling point of the reactants, a phenolic compound with dimethyl disulfide and a trialkyl phosphite each alkyl group thereof having from 1–12 carbon atoms, said phenolic compound being a phenol containing a ring substituent that is mercapto.

2. The process of claim 1 in which n is 1.

3. The process of claim 1 in which $R_1$ and $R_2$ are methyl or ethyl.

4. The process of claim 1 in which the trialkyl phosphite is trimethyl phosphite.

5. The process of claim 1 in which the trialkyl phosphite is triethyl phosphite.

6. The process of claim 1 in which the phosphate prepared is 0,0-dimethyl 0-(4-methylthiophenyl) phosphate by reaction of p-mercapto phenol with dimethyl disulfide and trimethyl phosphite.

7. The process of claim 1 comprising reacting said phenolic compound with said dimethyl disulfide and said trialkyl phosphite at a temperature of from about 30° to 60° C.

8. A process, as defined in claim 1, for selective preparation of 0,0-dialkyl phosphates of phenols having the following formula:

7

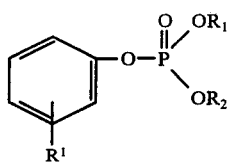

wherein R' is alkyl mercapto and R' and R² are alkyl of 1-12 carbon atoms which comprises reacting a phenol with a ring substituent that is p-mercapto with at least two mols of dimethyl disulfide and at least two mols of trialkyl phosphite, each alkyl group of which contains 1-12 carbon atoms, per mole of p-mercapto phenol.

* * * * *

8

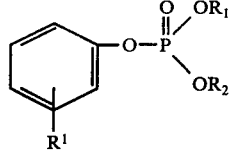

wherein R' is alkyl mercapto and R' and R² are alkyl of 1-12 carbon atoms which comprises reacting a phenol with a ring substituent that is p-mercapto with at least two mols of dimethyl disulfide and at least two mols of trialkyl phosphite, each alkyl group of which contains 1-12 carbon atoms, per mole of p-mercapto phenol.

* * * * *